United States Patent [19]
Southan et al.

[11] Patent Number: 6,100,059
[45] Date of Patent: Aug. 8, 2000

[54] COMPOUNDS

[75] Inventors: Christopher Donald Southan, Bishop's Stortford; Helen Elizabeth Clinkenbeard, Hertford; Nicola Anne Burgess, Edmonton, all of United Kingdom

[73] Assignee: SmithKline Beecham p.l.c., Middlesex, United Kingdom

[21] Appl. No.: 09/070,526

[22] Filed: Apr. 30, 1998

[30] Foreign Application Priority Data

Jan. 12, 1997 [EP] European Pat. Off. ............ 97309646
Jun. 9, 1997 [GB] United Kingdom ............ 9711952

[51] Int. Cl.$^7$ ................................... C12P 21/02
[52] U.S. Cl. ............... 435/69.1; 435/252.3; 435/320.1; 435/325; 435/455; 536/23.1; 536/23.2; 536/23.5
[58] Field of Search ............... 536/23.1, 23.5, 536/23.2; 435/317.1, 69.1, 325, 320.1, 455, 252.3

[56] References Cited

PUBLICATIONS

GenBank Accession #P00760.
GenBank Accession #P35033.
GenBank Accession #U62801.
GenBank Accession #D30785.
HGS EST #1703154.
GenBank Accession #A90164.
Critical Synergy: The Biotechnology Industry and Intellectual Property Protection, Biotechnology Industry Organization, Washingtion, DC, Oct. 17, 1994, pp. 75 and 100–107.

*Primary Examiner*—James Martinell
*Attorney, Agent, or Firm*—Elizabeth J. Hecht; Ratner & Prestia; William T. King

[57] ABSTRACT

HGBAB90 polypeptides and polynucleotides and methods for producing such polypeptides by recombinant techniques are disclosed. Also disclosed are methods for utilizing HGBAB90 polypeptides and polynucleotides in the design of protocols for the treatment of pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, among others, and diagnostic assays for such conditions.

12 Claims, No Drawings

COMPOUNDS

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to serine protease family, hereinafter referred to as HGBAB90. The invention also relates to inhibiting or activating the action of such polynucleotides and polypeptides.

BACKGROUND OF THE INVENTION

Proteases perform a variety of important functions in human physiology. Increasingly diseases are being identified where proteases are critical for the pathology of a particular disease. For these key proteases designing or screening for selective antagonists or agonists can lead to the development of new drugs. The serine proteases are a major family of proteases for which a large number are known. These have been reviewed by Rawlings & Barrett, (Methods Enzymol 244: 19–61, 1994). An example of the serine proteases is the mouse neuropsin (Chen et al. J Neurosci 15 (7 Pt 2): 5088–5097 1995).

There remains a need for identification and characterization of further members of the serine protease family which can play a role in preventing, ameliorating or correcting dysfunctions or diseases, including, but not limited to, pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy.

SUMMARY OF THE INVENTION

In one aspect, the invention relates to HGBAB90 polypeptides and recombinant materials and methods for their production. Another aspect of the invention relates to methods for using such HGBAB90 polypeptides and polynucleotides. Such uses include the treatment of pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, among others. In still another aspect, the invention relates to methods to identify agonists and antagonists using the materials provided by the invention, and treating conditions associated with HGBAB90 imbalance with the identified compounds. Yet another aspect of the invention relates to diagnostic assays for detecting diseases associated with inappropriate HGBAB90 activity or levels.

DESCRIPTION OF THE INVENTION

Definitions

The following definitions are provided to facilitate understanding of certain terms used frequently herein.

"HGBAB90" refers, among others, generally to a polypeptide having the amino acid sequence set forth in SEQ ID NO:2 or an allelic variant thereof.

"HGBAB90 activity or HGBAB90 polypeptide activity" or "biological activity of the HGBAB90 or HGBAB90 polypeptide" refers to the metabolic or physiologic function of said HGBAB90 including similar activities or improved activities or these activities with decreased undesirable side-effects. Also included are antigenic and immunogenic activities of said HGBAB90.

"HGBAB90 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- or double-stranded DNA, DNA that is a mixture of single- or double-stranded regions, single- or double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which were well known in the art. Such modifications are well described in basic tests and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62.

"Variant" as the term is used herein, as a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:

1) Algorithm: Needleman and Wunsch, J. Mol. Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol. Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

Polypeptides of the Invention

In one aspect, the present invention relates to HGBAB90 polypeptides (or HGBAB90 proteins). The HGBAB90 polypeptides include the polypeptide of SEQ ID NO:2; as well as polypeptides comprising the amino acid sequence of SEQ ID NO:2; and polypeptides comprising the amino acid sequence which have at least 75% identity to that of SEQ ID NO:2 over its entire length, more preferably at least 80% identity, still more preferably at least 90% identity, and even still more preferably at least 95% identity to SEQ ID NO:2. Furthermore, those with at least 97–99% are highly preferred. Also included within HGBAB90 polypeptides are polypeptides having the amino acid sequence which have at least 75% identity to the polypeptide having the amino acid sequence of SEQ ID NO:2 over its entire length, more preferably at least 80% identity, still more preferably at least 90% identity, and still more preferably at least 95% identity to SEQ ID NO:2. Furthermore, those with at least 97–99% are highly preferred. Preferably HGBAB90 polypeptide exhibit at least one biological activity of HGBAB90.

The HGBAB90 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine resides, or an additional sequence for stability during recombinant production.

Fragments of the HGBAB90 polypeptides are also included in the invention. A fragment is a polypeptide having an amino acid sequence that entirely is the same as part, but not all, of the amino acid sequence of the aforementioned HGBAB90 polypeptides. As with HGBAB90 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HGBAB90 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HGBAB90 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HGBAB90 activity, including those with a similar activity or an improved activity, or with a decreased undesirable activity. Also included are those that are antigenic or immunogenic in an animal, especially in a human.

Preferably, all of these polypeptide fragments retain the biological activity of the HGBAB90, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic resides Phe and Tyr. Particularly preferred are variants in which several 5–10, 1–5, or 1–2 amino acids are substituted, deleted, or added in any combination.

The HGBAB90 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HGBAB90 polynucleotides. HGBAB90 polynucleotides include isolated polynucleotides which encode the HGBAB90 polypeptides and fragments, and polynucleotides closely related thereto. More specifically, HGBAB90 polynucleotide of the invention include a polynucleotide comprising the nucleotide sequence contained in SEQ ID NO:1 encoding a HGBAB90 polypeptide of SEQ ID NO:2, and polynucleotides having the particular sequences of SEQ ID NOS:1 and 3. HGBAB90 polynucleotides further include a polynucleotide comprising a nucleotide sequence that has at least 80% identity over its entire length to a nucleotide sequence encoding the HGBAB90 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under HGBAB90 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such HGBAB90 polynucleotides.

HGBAB90 of the invention is structurally related to other proteins of the serine protease family, as shown by the results of sequencing the cDNA encoding human HGBAB90. The cDNA sequence of SEQ ID NO:1 contains an open reading frame (nucleotide number 105 to 888) encoding a polypeptide of 260 amino acids of SEQ ID NO:2. Amino acid sequence of SEQ ID NO:2 has about 73% identity (using BLASTX) in 254 amino acid residues with mouse neuropsin (Chen et al. J. Neurosci 15 (7 Pt 2): 5088–5097, 1995). Nucleotide sequence of SEQ ID NO:1 has about 76% identity (using BLAST) in 799 nucleotide residues with mouse mRNA for neuropsin (Chen et al. J Neurosci 15 (7 Pt 2): 5088–5097, 1995). Thus HGBAB90 polypeptides and polynucleotides of the present invention are expected to have, inter alia, similar biological functions/properties to their homologous polypeptides and polynucleotides, and their utility is obvious to anyone skilled in the art.

The present invention also relates to partial or other polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide comprising:
(a) a nucleotide sequence which has at least 80% identity, preferably at least 90% identity, more preferably at least 95% identity, most preferably at least 97–99% identity to SEQ ID NO:3 over the entire length of SEQ ID NO:3;
(b) a nucleotide sequence which has at least 80% identity, preferably at least 90% identity, more preferably at least 95% identity, even more preferably at least 97–99% identity to SEQ ID NO:3 over the entire length of SEQ ID NO:3;
(c) the polynucleotide of SEQ ID NO:3; or
(d) a nucleotide sequence encoding a polypeptide which has at least 80% identity, preferably at least 90% identity, more preferably at least 95% identity, yet more preferably at least 97–99% identity, to the amino acid sequence of SEQ ID NO:4, over the entire length of SEQ ID NO:4;
as well as the polynucleotide of SEQ ID NO:3.

The present invention further provides for a polypeptide which:
(a) comprises an amino acid sequence which has at least 80% identity, preferably at least 90% identity, more preferably at least 95% identity, most preferably at least 97–99% identity, to that of SEQ ID NO:4 over the entire length of SEQ ID NO:4;
(b) has an amino acid sequence which has at least 80% identity, preferably at least 90% identity, more preferably at least 95% identity, most preferably at least 97–99% identity, to the amino acid sequence of SEQ ID NO:4 over the entire length of SEQ ID NO:4;
(c) comprises the amino acid of SEQ ID NO:4; and
(d) is the polypeptide of SEQ ID NO:4;
as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognised by those skilled in the art that there will inevitably be come nucleotide sequence reading errors in EST sequences (see Adams, M.D. et al, Nature 377 (supp) 3, 1995). Accordingly, the nucleotide sequence of SEQ ID NO:3 and the peptide sequence encoded therefrom are therefore subjec to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

The cDNA sequence of SEQ ID NO:3 encodes polypeptides of SEQ ID NO:4. This sequence is compared with HGBAB90 and its closest homologous protein, human protease M (Anisowicz et al. Mol Med 2 (5): 624–636, 1996). Nucleotide sequence of SEQ ID NO:1 has about 77% identity (using BLASTN) in 148 nucleotide residues with mouse neuropsin (Chen et al. J Neurosci 15 (7 Pt 2): 5088–5097, 1995).

The present invention further relates to polynucleotides that hybridize to the herein above-described sequences. In this regard, the present invention especially related to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding HGBAB90 polypeptide and to isolate cDNA and genomic clones of other genes (including genes encoding homologs and orthologs from species other than human) that have a high sequence similarity to the HGBAB90 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HGBAB90 polypeptide, including homologs and orthologs from species other than human, comprises the steps of screening an appropriate library under stingent hybridization conditions with a labeled probe having the SEQ ID NO: 1 or a fragment thereof (including that of SEQ ID NO:3), and isolating full-length cDNA and genomic clones containing said polynucleotide sequence. Such hybridization techniques are well known to those of skill in the art. Thus in another aspect, HGBAB90 polynucleotides of the present invention further include a nucleotide sequence comprising a nucleotide sequence that hybridize under stringent condition to a nucleotide sequence having SEQ ID NO: 1 or a fragment thereof (including that of SEQ ID NO:3). Also included with HGBAB90 polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HGBAB90 polypeptide is to be expressed for use in screening assays, generally, it is preferred that the polypeptide be produced at the surface of the cell. In this event, the cells may be harvested prior to use in the screening assay. If HGBAB90 polypeptide is secreted into the medium, the medium can be recovered in order to recover and purify the polypeptide; if produced intracellularly, the cells must first be lysed before the polypeptide is recovered. HGBAB90 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HGBAB90 polynucleotides for use as diagnostic reagents. Detection of a mutated form of HGBAB90 gene associated with a dysfunction will provide a diagnostic tool that can add to or define a diagnosis of a disease or susceptibility to a disease which results from under-expression, over-expression or altered expression of HGBAB90. Individuals carrying mutations in the HGBAB90 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HGBAB90 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising HGBAB90 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy through detection of mutation in the HGBAB90 gene by the methods described.

In addition, pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, can be diagnosed by methods comprising determining from a sample derived from a subject an abnormally decreased or increased level of HGBAB90 polypeptide or HGBAB90 mRNA. Decreased or increased expression can be measured at the RNA level using any of the methods well known in the art for the quantitation of polynucleotides, such as, for example, PCR, RT-PRC, RNase protection, Northern blotting and other hybridization methods. Assay techniques that can be used to determine levels of a protein, such as an HGBAB90 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, which comprises:

(a) a HGBAB90 polynucleotide, preferably the nucleotide sequence of SEQ ID NO: 1, or a fragment thereof;
(b) a nucleotide sequence complementary to that of (a);
(c) a HGBAB90 polypeptide, preferably the polypeptide of SEQ ID NO: 2, or a fragment thereof; or
(d) an antibody to a HGBAB90 polypeptide, preferably to the polypeptide of SEQ ID NO: 2.

It will be appreciated that in any such kit, (a), (b), (c), or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic may data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

The HGBAB90 gene has been mapped to chromosome 19, 3.87 cR from NIB1805.

Antibodies

The polypeptides of the invention or their fragments or analogs thereof, or cells expressing them can also be used as immunogens to produce antibodies immunospecific for the HGBAB90 polypeptides. The term "immunospecific" means that the antibodies have substantial greater affinity for the polypeptides of the invention than their affinity for other related polypeptides in the prior art.

Antibodies generated against the HGBAB90 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HGBAB90 polypeptides may also be employed to treat pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, among others.

Vaccines

Another aspect of the invention relates to a method for inducing an immunological response in a mammal which comprises inoculating the mammal with HGBAB90 polypeptide, or a fragment thereof, adequate to produce antibody and/or T cell immune response to protect said animal from pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, among others. Yet another aspect of the invention relates to a method of inducing immunological response in a mammal which comprises delivering HGBAB90 polypeptide via a vector directing expression of HGBAB90 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HGBAB90 polypeptide wherein the composition comprises a HGBAB90 polypeptide or HGBAB90 gene. The vaccine formulation may further comprise a suitable carrier. Since HGBAB90 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HGBAB90 polypeptide of the present invention may be employed in a screening process for compounds which activate (agonists) or inhibit activation of (antagonists, or otherwise called inhibitors) the HGBAB90 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan et al., Current Protocols in Immunology 1(2):Chapter 5 (1991).

HGBAB90 polypeptides are responsible for many biological functions, including many pathologies. Accordingly, it is desirous to find compounds and drugs which stimulate HGBAB90 polypeptide on the one hand and which can inhibit the function of HGBAB90 polypeptide on the other hand. In general, agonists are employed for therapeutic and prophylactic purposes for such conditions as pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy. Antagonists may be employed for a variety of therapeutic and prophylactic purposes for such conditions as pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy.

In general, such screening procedures may involve using appropriate cells which express the HGBAB90 polypeptide or respond to HGBAB90 polypeptide of the present invention. Such cells include cells from mammals, yeast, Drosophila or *E. coli*. Cells which express the HGBAB90 polypeptide (or cell membrane containing the expressed polypeptide) or respond to HGBAB90 polypeptide are then contacted with a test compound to observe binding, or stimulation or inhibition of a functional response. The ability of the cells which were contacted with the candidate compounds is compared with the same cells which were not contacted for HGBAB90 activity.

The assays may simply test binding of a candidate compound wherein adherence to the cells bearing the HGBAB90 polypeptide is detected by means of a label directly or indirectly associated with the candidate compound or in an assay involving competition with a labeled competitor. Further, these assays may test whether the candidate compound results in a signal generated by activation of the HGBAB90 polypeptide, using detection systems appropriate to the cells bearing the HGBAB90 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a HGBAB90 polypeptide to form a mixture, measuring HGBAB90 activity in the mixture, and comparing the HGBAB90 activity of the mixture to a standard.

The HGBAB90 cDNA, protein and antibodies to the protein may also be used to configure assays for detecting the effect of added compounds on the production of HGBAB90 polypeptide mRNA and protein in cells. For example, an ELISA may be constructed for measuring secreted or cell associated levels of HGBAB90 protein using monoclonal and polyclonal antibodies by standard methods known in the art, and this can be used to discover agents which may inhibit or enhance the production of HGBAB90 (also called antagonist or agonist, respectively) from suitably manipulated cells or tissues.

The HGBAB90 protein may be used to identify membrane bound or soluble receptors, if any, through standard receptor binding techniques known in the art. These include, but are not limited to, ligand binding and crosslinking assays in which the HGBAB90 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of HGBAB90 which compete with the binding of HGBAB90 to its receptors, if any. Standard methods for conducting screening assays are well understood in the art.

Examples of potential HGBAB90 polypeptide antagonists include antibodies or, in some cases, oligonucleotides or proteins which are closely related to the ligands, substrates, enzymes, receptors, etc., as the case may be, of the HGBAB90 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for HGBAB90 polypeptides; or compounds which decrease or enhance the production of HGBAB90 polypeptides, which comprises:
(a) a HGBAB90 polypeptide, preferably that of SEQ ID NO:2;
(b) a recombinant cell expressing a HGBAB90 polypeptide, preferably that of SEQ ID NO:2;
(c) a cell membrane expressing a HGBAB90 polypeptide; preferably that of SEQ ID NO: 2; or
(d) antibody to a HGBAB90 polypeptide, preferably that of SEQ ID NO: 2.
It will be appreciated that in any such kit, (a), (b), (c) or (d) may comprise a substantial component.

Prophylactic and Therapeutic Methods

This invention provides methods of treating abnormal conditions such as, pulmonary emphysema, arthritis, multiple sclerosis, periodontal disease, cystic fibrosis, respiratory disease, thrombosis, cancer, cachexia, angina, glaucoma, inflamatory disorders, osteoporosis, cardiovascular disorders such as hypertension, atherosclerotic disorders such as cardiac infarction, and stroke, asthma, psoriasis, chronic neurodegenerative diseases such as Alzheimer's, Parkinson's, and Huntington's, demyelinating diseases, AIDS immune deficiency, disorders of photoreceptor degeneration, and lens cataract formation, organ transplant rejection, cataracts, restenosis, muscular dystrophy, renal failure, cerebral vasospasm, pancreatitis, and diabetic nephropathy, related to both an excess of and insufficient amounts of HGBAB90 polypeptide activity.

If the activity of HGBAB90 polypeptide is in excess, several approaches are available. One approach comprises administering to a subject an inhibitor compound (antagonist) as hereinabove described along with a pharmaceutically acceptable carrier in an amount effective to inhibit the function of the HGBAB90 polypeptide, such as, for example, by blocking the binding of ligands, substrates, enzymes, receptors, etc., or by inhibiting a second signal, and thereby alleviating the abnormal condition. In another approach, soluble forms of HGBAB90 polypeptides still capable of binding the ligand, substrate, enzymes, receptors, etc. in competition with endogenous HGBAB90 polypeptide may be administered. Typical embodiments of such competitors comprise fragments of the HGBAB90 polypeptide.

In another approach, soluble forms of HGBAB90 polypeptides still capable of binding the ligand in competition with endogenous HGBAB90 polypeptide may be administered. Typical embodiments of such competitors comprise fragments of the HGBAB90 polypeptide.

In still another approach, expression of the gene encoding endogenous HGBAB90 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of HGBAB90 and its activity, several approaches are also available. One approach comprises administering to a subject a therapeutically effective amount of a compound which activates HGBAB90 polypeptide, i.e., an agonist as described above, in combination with a pharmaceutically acceptable carrier, to thereby alleviate the abnormal condition. Alternatively, gene therapy may be employed to effect the endogenous production of HGBAB90 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of HGBAB90 polypeptides in combination with a suitable pharmaceutical carrier.

Formulation and Administration

Peptides, such as the soluble form of HGBAB90 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

All publications, including but not limited to patents and patent applications, cited in this specification are herein incorporated by reference as if each individual publication were specifically and individually indicated to be incorporated by reference herein as though fully set forth.

---

SEQ ID NO: 1[a]

---

AATTCGCCCTTACTCACTATAGGGCTCGAGCGGCCGCCCGGGCAGGTCTCCACTGGGTCCGAATCAGTAGGT

GACCCCGCCCCTGGATTCTGGAAGACCTCACCATGGGACGCCCCCGACCTCGTGCGGCCAAGACGTGGATGT

TCCTGCTCTTGCTGGGGGAGCCTGGGCAGGACACTCCAGGGCACAGGAGGACAAGGTGCTGGGGGGTCATG

AGTGCCAACCCCATTCGCAGCCTTGGCAGGCGGCCTTGTTCCAGGGCCAGCAAYTACTCTGTGGCGGTGTCC

TTGTAGGTGGCAACTGGGTCCTTACAGCTGCCCACTGTAAAAAACCGAAATACACAGTACGCCTGGGAGACC

ACAGCCTACAGAATAAAGATGGCCCAGAGCAAGAAATACCTGTGGTTCAGTCCATCCCACACCCCTGCTATA

ACAGCAGCGATGTGGAGGACCACAACCATGATCTGATGCTTCTTCAACTGCGTGACCAGGCATCCCTGGGGT

CCAAAGTGAAGCCCATCAGCCTGGCAGATCATTGCACCCAGCCTGGCCAGAAGTGCACCGTCTCAGGCTGGG

GCACTGTCACCAGTCCCCGAGAGAATTTTCCTGACACTCTCAACTGTGCAGAAGTAAAAATCTTTCCCCAGA

AGAAGTGTGAGGATGCTTACCCGGGGCAGATCACAGATGGCATGGTCTGTGCAGGCAGCAGCAAAGGGCTG

ACACGTGCCAGGGCGATTCTGGAGGCCCCCTGGTGTGTGATGGTGCACTCCAGGGCATCACATCCTGGGCT

CAGACCCCTGTGGGAGGTCCGACAAACCTGGCGTCTATACCAACATCTGCCGCTACCTGGACTGGATCAAGA

AGGGCGAAGGCAGCAAGGGCTGATTCTAGGATAAGCACTAGATCTCCCTTAATAAACTCACAACTTTCTGAA

AAAAAAAA

---

[a]A nucleotide sequence of a human HGBAB90.

---

SEQ ID NO: 2[b]

---

MGRPRPRAAKTWMFLLLLGGAWAGHSRAQEDKVLGGHECQPHSQPWQAALFQGQQLLCGGVLVGGNWVLTAA

HCKKPKYTVRLGDHSLQNKDGPEQEIPVVQSIPHPCYNSSDVEDHNHDLMLLQLRDQASLGSKVKPISLADH

CTQPGQKCTVSGWGTVTSPRENFPDTLNCAEVKIFPQKKCEDAYPGQITDGMVCAGSSKGADTCQGDSGGPL

VCDGALQGITSWGSDPCGRSDKPGVYTNICRYLDWIKKGEGSKG

---

[b]An amino acid sequence of a human HGBAB90.

What is claimed is:

1. An isolated polynucleotide comprising a nucleotide sequence encoding the HGBAB90 polypeptide of SEQ ID NO:2.

2. The polynucleotide of claim 1 wherein said polynucleotide comprises the nucleotide sequence of SEQ ID NO:1.

3. The isolated polynucleotide of claim 2 comprising nucleotides 105 to 888 of the polynucleotide of SEQ ID NO:1.

4. An expression vector comprising a polynucleotide encoding a HGBAB90 polypeptide comprising the amino acid sequence of SEQ ID NO:2 when said expression vector is present in a compatible host cell.

5. A host cell comprising the expression vector of claim 4.

6. A process for producing a HGBAB90 polypeptide comprising culturing the host of claim 5 under conditions sufficient for the production of said polypeptide and recovering said polypeptide from the culture.

7. A process for producing a cell which produces a HGBAB90 polypeptide thereof comprising transforming or transfecting a host cell with the expression vector of claim 4 such that the host cell, under appropriate culture conditions, produces a HGBAB90 polypeptide.

8. A recombinant host cell produced by the process of claim 7.

9. An isolated polynucleotide comprising an RNA sequence corresponding to nucleotides 105 to 888 of the nucleotide sequence of SEQ ID NO:1.

10. The isolated polynucleotide of claim 9 comprising an RNA sequence corresponding to the entire length of the nucleotide sequence of SEQ ID NO:1.

11. An isolated polynucleotide which is complementary to a nucleotide sequence encoding the amino acid sequence of SEQ ID NO:2.

12. The isolated polynucleotide of claim 11 which is complementary to the nucleotide sequence of SEQ ID NO:1.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 944 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
AATTCGCCCT TACTCACTAT AGGGCTCGAG CGGCCGCCCG GGCAGGTCTC CACTGGGTCC      60

GAATCAGTAG GTGACCCCGC CCCTGGATTC TGGAAGACCT CACCATGGGA CGCCCCCGAC     120

CTCGTGCGGC CAAGACGTGG ATGTTCCTGC TCTTGCTGGG GGGAGCCTGG GCAGGACACT     180

CCAGGGCACA GGAGGACAAG GTGCTGGGGG GTCATGAGTG CCAACCCCAT TCGCAGCCTT     240

GGCAGGCGGC CTTGTTCCAG GGCCAGCAAY TACTCTGTGG CGGTGTCCTT GTAGGTGGCA     300

ACTGGGTCCT TACAGCTGCC CACTGTAAAA AACCGAAATA CACAGTACGC CTGGGAGACC     360

ACAGCCTACA GAATAAAGAT GGCCCAGAGC AAGAAATACC TGTGGTTCAG TCCATCCCAC     420

ACCCCTGCTA TAACAGCAGC GATGTGGAGG ACCACAACCA TGATCTGATG CTTCTTCAAC     480

TGCGTGACCA GGCATCCCTG GGGTCCAAAG TGAAGCCCAT CAGCCTGGCA GATCATTGCA     540

CCCAGCCTGG CCAGAAGTGC ACCGTCTCAG GCTGGGGCAC TGTCACCAGT CCCCGAGAGA     600

ATTTTCCTGA CACTCTCAAC TGTGCAGAAG TAAAAATCTT TCCCCAGAAG AAGTGTGAGG     660

ATGCTTACCC GGGGCAGATC ACAGATGGCA TGGTCTGTGC AGGCAGCAGC AAAGGGGCTG     720

ACACGTGCCA GGGCGATTCT GGAGGCCCCC TGGTGTGTGA TGGTGCACTC CAGGGCATCA     780

CATCCTGGGG CTCAGACCCC TGTGGGAGGT CCGACAAACC TGGCGTCTAT ACCAACATCT     840

GCCGCTACCT GGACTGGATC AAGAAGGGCG AAGGCAGCAA GGGCTGATTC TAGGATAAGC     900

ACTAGATCTC CCTTAATAAA CTCACAACTT TCTGAAAAAA AAAA                      944
```

(2) INFORMATION FOR SEQ ID NO:2:

(i) SEQUENCE CHARACTERISTICS:
       (A) LENGTH: 260 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:2:

```
Met Gly Arg Pro Arg Pro Arg Ala Ala Lys Thr Trp Met Phe Leu Leu
1               5                   10                  15

Leu Leu Gly Gly Ala Trp Ala Gly His Ser Arg Ala Gln Glu Asp Lys
                20                  25                  30

Val Leu Gly Gly His Glu Cys Gln Pro His Ser Gln Pro Trp Gln Ala
            35                  40                  45

Ala Leu Phe Gln Gly Gln Gln Leu Leu Cys Gly Gly Val Leu Val Gly
        50                  55                  60

Gly Asn Trp Val Leu Thr Ala Ala His Cys Lys Lys Pro Lys Tyr Thr
65                  70                  75                  80
```

```
Val Arg Leu Gly Asp His Ser Leu Gln Asn Lys Asp Gly Pro Glu Gln
             85                  90                  95

Glu Ile Pro Val Val Gln Ser Ile Pro His Pro Cys Tyr Asn Ser Ser
            100                 105                 110

Asp Val Glu Asp His Asn His Asp Leu Met Leu Leu Gln Leu Arg Asp
            115                 120                 125

Gln Ala Ser Leu Gly Ser Lys Val Lys Pro Ile Ser Leu Ala Asp His
130                 135                 140

Cys Thr Gln Pro Gly Gln Lys Cys Thr Val Ser Gly Trp Gly Thr Val
145                 150                 155                 160

Thr Ser Pro Arg Glu Asn Phe Pro Asp Thr Leu Asn Cys Ala Glu Val
            165                 170                 175

Lys Ile Phe Pro Gln Lys Lys Cys Glu Asp Ala Tyr Pro Gly Gln Ile
            180                 185                 190

Thr Asp Gly Met Val Cys Ala Gly Ser Ser Lys Gly Ala Asp Thr Cys
            195                 200                 205

Gln Gly Asp Ser Gly Gly Pro Leu Val Cys Asp Gly Ala Leu Gln Gly
210                 215                 220

Ile Thr Ser Trp Gly Ser Asp Pro Cys Gly Arg Ser Asp Lys Pro Gly
225                 230                 235                 240

Val Tyr Thr Asn Ile Cys Arg Tyr Leu Asp Trp Ile Lys Lys Gly Glu
            245                 250                 255

Gly Ser Lys Gly
            260
```

(2) INFORMATION FOR SEQ ID NO:3:

(i) SEQUENCE CHARACTERISTICS:
        (A) LENGTH: 346 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
CAGAGAGTTG TGAGTTTATT AAGGGAGATC TAGTGCTTAT CCTAGAATCA GCCCTTGCTG      60
CCTATGATCT TCTTGATCCA GTCCAGGTAG CGGCAGATGT TGGTAGAGAC GCCAGGTTTG     120
TCGGACCTCC CACAGGGGTC TGAGCCCCAG GATGTGATGC CCTGGAAGTG CACCATGCAC     180
ACACCAGGGG GCCTCCAGAA TCGCCCTAGA CAGGGAGAAT GAGAACAGCC TTGCATCTGA     240
GATGTCCACA ACGTCCCTTT TCCTGCTGTC CCAGCGTTTT ACCAGTTCTT TGGCATGATT     300
GGTCCCCTGT AGCCAATGGG GGTAAAAGCA TTGTCCCCTG AGACCA                    346
```

(2) INFORMATION FOR SEQ ID NO:4:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

-continued

```
Pro Gly Val Cys Met Val His Phe Gln Gly Ile Thr Ser Trp Gly Ser
1               5                   10                  15

Asp Pro Cys Gly Arg Ser Asp Lys Pro Gly Val Ser Thr Asn Ile Cys
            20                  25                  30

Arg Tyr Leu Asp Trp Ile Lys Lys Ile Ile Gly Ser Lys
            35              40              45
```